(12) United States Patent
Zhang et al.

(10) Patent No.: US 9,920,094 B2
(45) Date of Patent: Mar. 20, 2018

(54) AFFINITY PEPTIDE LIGAND OF MOUSE POLYOMA VIRUS CAPSOMER AND DESIGNED SCREENING METHOD THEREOF

(71) Applicant: TIANJIN UNIVERSITY, Tianjin (CN)

(72) Inventors: Lin Zhang, Tianjin (CN); Xiaoyan Dong, Tianjin (CN); Yanying Li, Tianjin (CN); Xiaodan Liu, Tianjin (CN); Yan Sun, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 15/320,008

(22) PCT Filed: Nov. 10, 2014

(86) PCT No.: PCT/CN2014/090715
§ 371 (c)(1),
(2) Date: Dec. 19, 2016

(87) PCT Pub. No.: WO2015/192589
PCT Pub. Date: Dec. 23, 2015

(65) Prior Publication Data
US 2017/0129922 A1 May 11, 2017

(30) Foreign Application Priority Data
Jun. 19, 2014 (CN) .......................... 2014 1 0276200

(51) Int. Cl.
*C07K 7/06* (2006.01)
*G06F 19/16* (2011.01)

(52) U.S. Cl.
CPC ................ *C07K 7/06* (2013.01); *G06F 19/16* (2013.01)

(58) Field of Classification Search
None
See application file for complete search history.

(56) References Cited

FOREIGN PATENT DOCUMENTS

| CN | 101812129 A | 8/2010 |
|---|---|---|
| CN | 103145804 A | 6/2013 |

OTHER PUBLICATIONS

Apr. 8, 2015 Office Action issued in Chinese Patent Application No. 201410276200.X.
Nov. 13, 2015 Office Action issued in Chinese Patent Application No. 201410276200.X.
Mar. 27, 2015 International Search Report issued in International Patent Application No. PCT/CN2014/090715.

*Primary Examiner* — Christopher M Gross
(74) *Attorney, Agent, or Firm* — Oliff PLC

(57) ABSTRACT

Affinity peptide ligands of mouse polyomavirus capsomers and a designed screening method thereof. The affinity peptide ligands can be used for separation and purification of the capsomers.

11 Claims, 1 Drawing Sheet

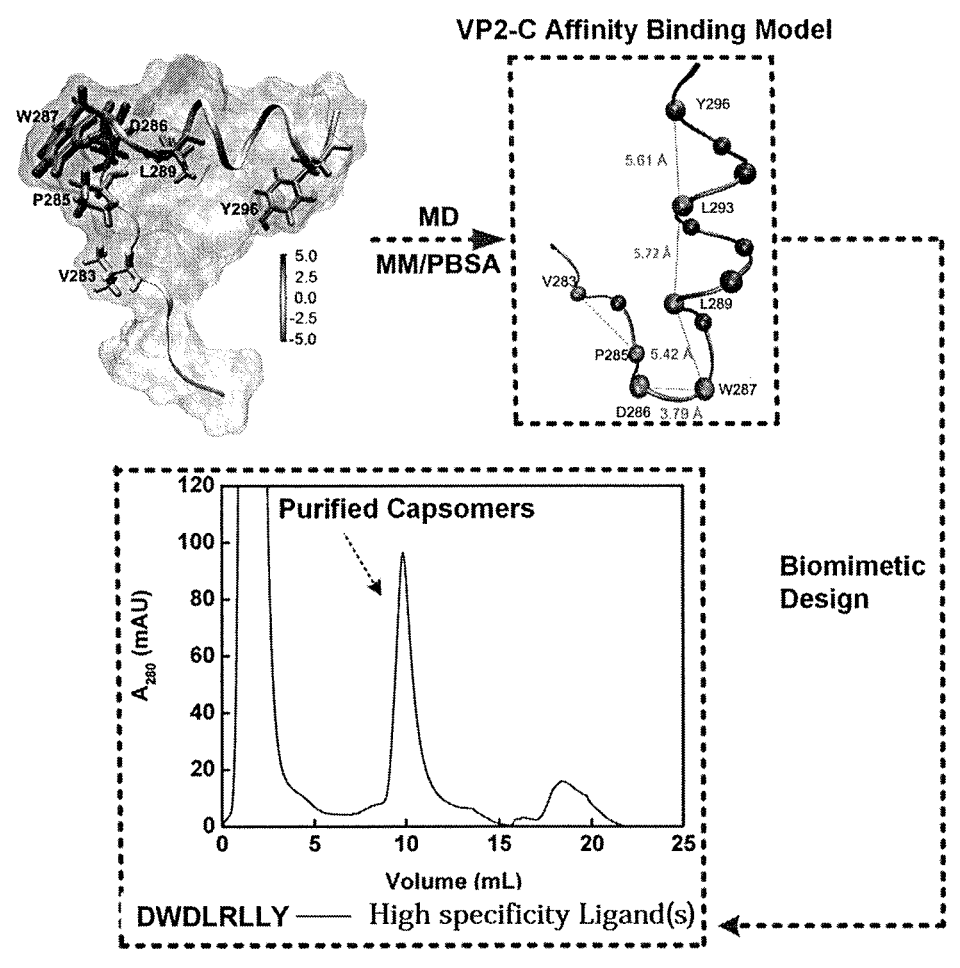

VP2-C Affinity Binding Model

AFFINITY PEPTIDE LIGAND OF MOUSE POLYOMA VIRUS CAPSOMER AND DESIGNED SCREENING METHOD THEREOF

TECHNICAL FIELD

The present invention relates to technology of design of affinity peptide ligands for target protein using in silico simulations, and purification of the target protein by affinity chromatography. The invention belongs to the technical field of in silico simulations and protein separation and purification in biotechnology.

BACKGROUND

A mouse polyomavirus (MPV) virus-like particle (VLP) is a hollow nanoparticle formed by self-assembly of major coat protein VP1 (42 kDa) and has great potential in vaccinology, gene therapy, drug delivery, and materials science. MPV VLP consists of 72 capsomers (Caps) positioned at a T=7d lattice inclining to the right, each of which comprises five VP1 molecules.

VP1, purified after expression in prokaryotic cells, can exist as Cap and self-assembles into VLP which is homogeneous in formation and stable in structure under proper in-vitro conditions. This in-vitro VLP production method has a broad application prospect for reasons of simplicity and efficiency. To date, a yield of up to 4.38 g $L^{-1}$ of VP1 with an N-terminal GST tag has been achieved from a pH-stat fed-batch high-cell-density process. While the GST tag could enhance the soluble expression of VP1 protein and improve the ease of tagged precursor purification, the subsequent enzymatic removal of the GST tag with expensive thrombin followed by additional separation and purification of the removed GST tag from the reaction system leads to complex operation and high cost, which present a daunting challenge in the expansion of production, thus limiting the applications of MPV VLP.

Affinity chromatography capable of separating and purifying a target molecule by interaction between biomacromolecules and specificity ligands is advantaged by high selectivity, high efficiency, mild operating condition, etc. The ligand is crucial for affinity chromatography as the realization of affinity chromatography depends on the specificity identification between the target molecule and the ligand. Peptide ligands have a significant development prospect for their high affinity, high stability, little proneness to degradation, simple production, and the like. With the rapid development of molecular simulations in recent years, designed screening has been achieved for high-specificity affinity peptide ligands by simulating target protein-ligand interactions that have already existed in natural world, and thus the screening efficiency and accuracy of the affinity peptide ligands are improved.

A MPV Cap and minor coat protein VP2 (35 kDa) complex is a naturally-existing Cap-ligand complex. The C-terminus of VP2 (thereafter termed VP2-C) binds in an unusual, hairpin-like manner into the inner surface of Cap through hydrophobic interactions. Herein a design basis of affinity peptide ligands of Caps has been developed.

SUMMARY

The purpose of the invention is to bring forward applications of a designing and screening method of novel affinity peptide ligands for MPV Caps. This biomimetic design process for affinity peptide ligands for Caps is established for the first time and is verified to be feasible. These affinity peptide ligands have the advantage of high specificity, good stability and ease of operation.

The technical scheme of the invention is as follows:

The novel affinity peptide ligands for MPV Caps are: DWDLRLLY, DWDLRLIY, DWNLRLIY, DWFLNLFY, DWSLKLVY, DWSLRLKY and DWNLHLPY.

According to the novel affinity peptide ligands of MPV Caps and the designed screening method thereof in the invention, a novel peptide ligand library of Caps is constructed on the basis of the crystal structure of a Cap and VP2-C complex existing in the natural world, with the feature sequence being DWXLXLXY, wherein the 'X' denotes 19 amino acids except cysteine; and the sequence is as shown in a nucleotide sequence list.

The molecular interaction mechanism of the Cap and VP2-C complex is examined using a molecular mechanics-Poisson-Boltzmann surface area (MM/PBSA) method, where hydrophobic interaction is identified as the major driving force while V283, P285, D286, W287, L289, L293, and Y296 are identified as key residues, making significant contribution to binding, in VP2-C.

The peptide library is constructed on the basis of five key residues in VP2-C, i.e., D286, W287, L289, L293, and Y296; and within the range of the peptide library, a candidate peptide modular library is constructed using an amino acid locating method. The high-affinity peptide ligands of MPV Caps are screened by molecular docking screening, root-mean-square deviation (RMSD) comparison, and molecular dynamics (MD) simulation coupled with free energy calculation.

The peptide ligands from the peptide ligand library are sequentially docked to MPV Caps using molecular docking software VINA and a total of 1158 peptide ligands with binding free energy less than −6.5 kcal/mol are selected.

The RMSD values between the 1158 peptide ligands obtained from docking by VINA and the corresponding key residues in VP2-C are calculated by a program g_rms provided by molecular simulation software GROMACS, and 334 peptide ligands are selected for researching.

The 334 peptide ligands are then rescreened on the basis of the C-terminus orientation. 227 peptide ligands having the similar orientation with VP2-C are selected and rescreened by a docking experiment ROSETTA FlexPepDock. The ten optimal peptide ligands are then selected for MD simulations.

The ten peptide ligands obtained by screening are subjected to MD simulations with the complex of MPV Caps, and free energy calculation is conducted using the MM/PBSA method to further evaluate the affinity and specificity of the peptide ligands, thereby obtaining seven peptide ligands with relatively high affinity, which are DWDLRLLY, DWDLRLIY, DWNLRLIY, DWFLNLFY, DWSLKLVY, DWSLRLKY and DWNLHLPY.

In this invention, 1) the feature sequence is DWXLXLXY, where the 'X' denotes 19 amino acids except cysteine, and 2) the peptide library is built on the basis of five key residues in VP2-C, i.e., D286, W287, L289, L293, and Y296, and within the range of the peptide library, a candidate peptide modular library is constructed using an amino acid locating method. A modification strategy for the ligand peptide library includes: adding one or more amino acid residues to the N-terminus; introducing one or more amino acid residues to the C-terminus; inserting one or more amino acid residues between adjacent residues of the peptides; replacing certain one or more resides in the peptides with other amino acid residues.

The detailed descriptions of this invention are given as follows:

In the invention, the novel affinity peptide ligand library for Caps is built on the basis of a VP2-C affinity binding model, where five key residues, i.e., D286, W287, L289, L293 and Y296, of VP2-C are the basis. The sequence feature of the peptide library is DWXLXLXY, where the 'X' denotes 19 amino acids except cysteine.

The peptide library is then screened by VINA docking, RMSD comparison, C-terminus orientation comparison, and ROSETTA FlexPepDock docking and rescreened by MD simulations coupled with free energy calculation. Seven peptide ligands with relatively high affinity towards Caps are obtained: DWDLRLLY, DWDLRLIY, DWNLRLIY, DWFLNLFY, DWSLKLVY, DWSLRLKY and DWNLHLPY. The top one ligand DWDLRLLY has been experimentally validated to be an effective affinity ligand of Caps.

It should be noted that, although virtual screening could effectively and accurately shrink the number of relatively high affinity peptides, the prediction of the intermolecular interaction has not yet been completely in line with the actual situation due to the limitations of in silico simulations (e.g., the different software or parameters adopted may lead to different results). Thus, the peptides with relatively high affinity and specificity may be missed in the actual screening process. As a result, it cannot be rule out that the other 6852 peptide molecules in the peptide library are also likely affinity peptide ligands of Caps.

The method that this invention utilized to obtain affinity peptide ligands of Caps by molecular simulations and chromatography experiments is shown in FIG. 1 and characterized by comprising the following process:

1. The relative binding free energy of the Cap and VP2-C complex (the crystal structure was taken from PDB: 1CN3) is calculated using MD simulations coupled with the MM/PBSA method. Free energy decomposition is adopted to study the binding interactions between VP2-C and Caps and to analyze and determine the hot spot residues of VP2-C. According to the molecular interactions and the spatial distribution features of the residues, a simplified affinity binding model of VP2-C is constructed.

2. According to the conformation and relative positions of the five hot spot residues (D286, W287, L289, L293 and Y296) located on an α-helix in VP2-C, a peptide library of peptides with the sequence mode being DWXLXLXY is determined using an amino acid locating method, where X stands for 19 arbitrary amino acids except for cysteine. A perl script invoking CHARMM is used to build the peptide library comprising 6859 peptides.

3. The docking software VINA is chosen for docking the 6859 peptide ligands in the peptide library to the binding regions of the inner cavity surface of Caps successively, and then a total of 1158 peptides with binding free energy (rating scores) less than −6.5 kcal/mol are selected according to the distribution of the rating scores. The RMSD values between the five hot spot residues in VP2-C and those corresponding in the 1158 peptide sequences obtained by docking are calculated sequentially by the program g_rms provided by the GROMACS 4.5.3 simulation package. Herein, the conformations of the hot spot residues in VP2-C and those corresponding in the peptides after VINA docking are compared. The smaller the RMSD value, the more alike the two conformations of the corresponding hot spot residues are. 334 peptides with RMSD values less than 0.4 nm are selected according to the distribution of the RMSD values for further study. In the crystal structure of the Cap and VP2-C complex, the C-terminus of VP2-C is located at the bottom of Cap. Then the peptides without similar C-terminus orientation with VP2-C, e.g., with N-terminus toward the bottom of Cap, are not considered in the following screening. Then 227 peptides are selected for next screening. The selected peptides are then rescreened by flexible molecular docking on a ROSETTA FlexPepDock web server (http://flexpepdock.furmanlab.cs.huji.ac.il/). The default docking parameters are used. Every peptide and Cap complex generates 200 conformations in total. The top ten peptides with high score (the binding interface energy score I_sc) are considered for further study.

4. Ten conformations of the peptide and Cap complex obtained from ROSETTA FlexPepDock docking in the step 3 are set as the initial conformations. MD simulations are performed using the GROMACS 4.5.3 package with a CHARMM27 force field. The peptide and Cap complex is first placed in the center of a cubic box (12.16×12.16×12.16 nm$^3$), and the water molecular model is the TIP 3P model. Then Na$^+$ and Cl$^-$ are added as required for neutralization of net charge of the system and a buffer (200 mM NaCl) solution. After that, energy minimization is conducted to remove atom clashes and incorrect geometrical conformations in the system. Then the system is equilibrated for 200 ps under NVT ensemble and further 200 ps under NPT ensemble. At last, the unconstrained MD simulation is carried out for 20 ns. The final binding conformations of the ten peptides in MD simulations are compared to the original conformation. After the simulation, the last 3 ns trajectory of simulation are extracted and calculated by the MM/PBSA method for free energy calculation to further evaluate the affinity and specificity of the peptides. It is shown that seven peptides (DWDLRLLY, DWDLRLIY, DWNLRLIY, DWFLNLFY, DWSLKLVY, DWSLRLKY and DWNLHLPY) are predicated to have high affinity towards Cap.

5. The top one peptide DWDLRLLY is immobilized onto a Thiopropyl Sepharose 6B chromatography medium to prepare an affinity medium. A series of experimental methods including protein static adsorption, affinity chromatography and sodium dodecyl sulfate polyacrylamide gel electrophoresis (SDS-PAGE) are conducted to validate that the DWDLRLLY is an effective affinity ligand of Cap.

In this invention, the hot spot residues of VP2-C with high affinity for Caps are first examined using MD simulations coupled with the MM/PBSA method, leading to a simplified VP2-C affinity binding model of Cap. On the basis of the model, an affinity peptide library of Caps is then constructed. Thereafter, molecular docking and MD simulation coupled with free energy calculation are used to screen the peptide library and a pool of peptide ligands of high affinity for Caps is obtained. A series of experimental methods including protein static adsorption, affinity chromatography, SDS-PAGE are conducted to investigate the Cap separation and purification efficiency of the obtained ligands. The top one ligand DWDLRLLY is validated to be capable of separating and purifying Caps effectively and is also advantaged by high specificity, good stability, and ease of operation, which indicates the feasibility of biomimetic design strategy of the affinity peptide ligands. However, it should be noted that there also exist some problems in DWDLRLLY, such as too strong hydrophobicity, in actual use. Thereafter, to obtain more affinity and specific peptide ligands, modifications of the DWDLRLLY and other peptides in the library are required in the following experiments. A modification strategy for the ligand peptide library includes: adding one or more amino acids to the N/C-terminus of the peptides; inserting one or more amino acids between adjacent residues in the peptides; and replacing certain one or more residues in the peptides with other amino acids.

BRIEF DESCRIPTION OF THE DRAWINGS

FIG. 1 is a chart of a design and screening strategy of novel affinity peptide ligands of MPV Cap.

DETAILED DESCRIPTION

Combined with the specific embodiments, the followings are the further description of the invention in detail.

Embodiment 1. Affinity Interaction Analysis Between VP2-C and Caps and Construction of a VP2-C Simplified Affinity Binding Model The crystal structure of a Cap and VP2-C complex, adopted in the invention, is taken from the Protein Data Bank (PDB ID: 1CN3, http://www.rcsb.org/pdb/). Cap comprises five VP1 (residues from 34-316) while VP2-C contains 19 residues (residues from 279 to 297). In this work, MD simulations are performed using a GROMACS 4.5.3 package with an all-atom CHARMM27 force field. The Cap and VP2-C complex is first solvated in a cubic box (12.163× 12.163×12.163 nm) using TIP3P as the water model. 225 $Na^+$ and 190 $Cl^-$ are added. After energy minimization, the system is equilibrated for 200 ps under NVT ensemble and further 200 ps under NPT ensemble. The temperature of the system is controlled at 298.15 K by the velocity-rescale (V-rescale) method. Periodic boundary conditions are adopted for all the simulations. The calculation of nonbinding interactions adopts 1.2 nm cut-off. The long-range electrostatic interactions are treated with the particle mesh Ewald (PME) method. All hydrogen atoms are constrained with the Lincs algorithm with a 2 fs time step. The simulation is carried out for 20 ns.

The RMSD and the potential energy of the complex reach equilibrium at a time scale of 5 ns according to the simulation result. Therefore, 75 snapshots of conformations extracted from the 17-20 ns trajectory of the complex at an interval of 40 ps are collected for the calculation and analysis of free energy. The hydrophobic interaction contribution of the Cap and VP2-C complex is −79 kcal/mol while the electrostatic interaction contribution is 3 kcal/mol, which indicates that the major driving force for affinity between Cap and VP2-C is hydrophobic interaction, which is in line with experimental facts in terms of the X-ray crystal diffraction structure. For electrostatic interaction, most intermolecular electrostatic interaction contribution (−171 kcal/mol) favorable for molecular binding is compensated by the unfavorable electrostatic solvation interaction energy (177 kcal/mol). So the total electrostatic interaction energy is very small relatively.

The free energy decomposition of VP2-C in the Cap and VP2-C complex is utilized to identify the hot spot residues. In this invention, the hot spot residues are identified as the residues that have large contribution to the binding free energy and that are involved in the important intermolecular interaction formation to compensate the unfavorable solvation interaction. The residues contributing a lot to the free energy are identified on the basis of the criterion of ±2.5 kcal/mol. For VP2-C, six hot spot residues (V283, P285, D286, W287, L289 and Y296) are found in calculation. It should be noted that the contribution of L293 to the free energy is not satisfied with the criterion of the hot spot residues. It is reported that the mutation L181E on simian virus 40 (SV40) minor coat protein VP3 causes reduction of VP3 and Cap binding by 33%, where L181 in SV40 VP3 is just the counterpart of L293 in MPV VP2 herein. Therefore, in consideration of the high conserved region in polyomaviruses, L293 is considered to be important in the binding of VP2-C and Cap and thus included in the process of construction of the affinity binding model. Finally, the VP2-C simplified affinity binding model is construction according to the affinity mechanism of VP2-C and Cap and the distribution of the hot spot residues of VP2-C, and comprises V283, P285, D286, W287, L289, L293 and Y296.

Embodiment 2. Construction of Polypeptide Library

The key residues, i.e., D286, W287, L289, L293 and Y296, located nearest to the base of Cap, were selected as the starting point of polypeptide construction, thereby maximally avoiding the steric-hindrance effect existing in the actual operation. W287, L289, L293 and Y296 are almost aligned in a straight line, which is favorable for the design of short peptide ligands without needing consideration of the spatial conformations of VP2. It is known that the lengths of a peptide bond and an amino acid backbone are about 1.33 Å and 2.78 Å, respectively. The insertion of one amino acid reside requires the lengths of two peptide bonds and the length of one amino acid backbone, i.e., about 2×1.33+ 2.78=5.44 Å. The VMD calculation obtains the results that W287–L289=5.42 Å, L289–L293=5.72 Å, and L293– Y296=5.61 Å. Accordingly, one amino acid can be inserted between every two adjacent hot spot residues. Thus, an octapeptide library of DWXLXLXY, where "X" represents residues (except Cys), containing 6859 sequences, each having the aforementioned five hot spot residues, is rationally designed and constructed finally by CHARMM invoked by a perl script.

Embodiment 3. Docking of Peptides to Caps

1. VINA Docking 6859 peptides are first docked into the binding region located on the inner cavity surface of Caps using VINA and ranked from −4 to −8 kcal/mol, which is in line with the requirement that affinity ligands should have medium affinity (the binding constant is in the range of $10^4$-$10^8$ $M^{-1}$). Then, in order to avoid missing the promising ligands, 1158 peptide candidates with the binding free energy being less than −6.5 kcal/mol are selected according to the empirical value and distribution result.

2. RMSD Calculation

The program g_rms provided by the GROMACS 4.5.3 simulation package is used to calculate the RMSD values between the hot spot residues in the 1158 peptide sequences obtained by VINA docking and those corresponding in Cap. Smaller RMSD value indicates higher structure similarity of the docked conformation of the hot spot residues contained in the peptides to the conformation of those corresponding in VP2-C. The results show that the distribution of RMSD is in the range of 0.3-0.6 nm, and 334 peptide sequences with RMSD values less than 0.4 nm are selected for the next step of analysis.

3. C-Terminus Orientation Comparison

In the Cap and VP2-C complex, the VP2-C runs from the bottom to the top of the inner cavity of Cap and the C-terminus is thus located at the bottom of Cap. Then the peptides without similar orientation with VP2-C, e.g., with N-terminus toward the bottom of Cap, are not considered in the following screening. Then 227 peptides are selected for next screening.

4. Rescreening Peptides Using FlexPepDock

The selected peptides are then rescreened by using a ROSETTA FlexPepDock web server. FlexPepDock mainly consists of two modules that optimize the peptide backbone and rigid body orientation, respectively. The starting structure is refined in 200 independent FlexPepDock simulations. 100 of the simulations are carried out strictly in a high-resolution mode, while 100 of the simulations include a low-resolution pre-optimization step, followed by the high-resolution refinement. A total of 200 models are thus created and then ranked based on their generic full-atom energy scores. 10 optimal conformations for each peptide are created. The top ten peptides with high scoring function scores are finally screened out, i.e., DWDLRLLY, DWDLRLIY, DWGLRLKY, DWSLKLVY, DWFLNLFY, DWSLDLWY, DWGLKLIY, DWNLRLIY, DWSLRLKY and DWNLHLPY.

Embodiment 4. MD Simulations and MM/PBSA Free Energy Calculation

To further predict the affinity interaction between Caps and the peptide ligand complex more precisely by using computer-aided ligand design, MD simulations coupled with free energy calculation with more calculation but also more accuracy are utilized to further evaluate the magnitude of affinity of the complex. The MD simulation parameters are in accordance with the embodiment 1. The final and original conformations of the peptides are compared using VMD. It is shown that except DWGLKLIY, DWGLRLKY and DWSLDLWY, the other seven peptides (DWDLRLLY, DWDLRLIY, DWSLKLVY, DWFLNLFY, DWNLRLIY, DWSLRLKY, and DWNLHLPY) keep a stable binding conformation with Caps during the MD simulations and thereby are predicated to be effective affinity ligands of Caps.

The binding free energies of these peptide ligands on the inner surface of Caps are calculated by MM/PBSA and the results are listed according to the binding free energies from high to low: DWDLRLLY, DWDLRLIY, DWNLRLIY, DWFLNLFY, DWSLKLVY, DWSLRLKY, DWNLHLPY, DWSLDLWY, DWGLRLKY, DWGLKLIY. The last three peptides present three ligands with unstable binding conformations with Caps during the MD simulations. For binding of all the ten peptides with Caps, the free energy calculation results indicate that the hydrophobic interaction contribution is dominant, which is in agreement with the initial design thinking, demonstrating the accuracy of rational design. The optimal peptide is DWDLRLLY according to the free energy calculation, as it has a binding free energy of −61 kcal/mol with Caps, close to the binding free energy (−76 kcal/mol) of VP2-C with Caps. Thus, DWDLRLLY is considered as the high-specificity affinity ligand of Caps.

Embodiment 5. Affinity Chromatography Experiment Validation

1. Preparation of Affinity Medium DWDLRLLY-6B and *E. coli* Lysate

A Thiopropyl Sepharose 6B (GE Healthcare) medium is washed with transmembrane water and then pre-equilibrated in linking buffer (0.5 M NaCl, 1 mM EDTA, 0.1 M PBS, pH 6.5) for 12 h. After being drained, 1 g of the wet medium is transferred into an Erlenmeyer flask containing 2.57 mg of peptides and 10 mL of linking buffer. After fully mixed, the mixture reacts in a shaking bath at 25° C. and 170 rpm for 2 h. The affinity peptide medium with the ligand density being 2 μmol/(g drained wet medium) (thereafter termed DWDLRLLY-6B) is obtained.

A plasmid pGEX-Ssp DnaB-Ser-VP1 is constructed and transformed into *E. coli* BL21(DE3). The recombinant *E. coli* BL21(DE3) is inoculated in 25 mL of TB medium [100 mg/L ampicillin, 12 g/L tryptone, 24 g/L yeast extract, 0.4% (v/v) glycerol, 2.31 g/L $KH_2PO_4$, 12.54 g/L $K_2HPO_4$] overnight at 37° C., 170 rpm. Then the culture is diluted 1:1000 in 250 mL TB medium and grown to $OD_{600}$≈0.5-0.6 (37° C., 170 rpm), after which protein expression is induced for 24 h by the addition of 0.3 mM IPTG at 26° C., 170 rpm. The cell pellets from 250 mL of the fermentation broth are harvested, re-suspended and lysed by sonication on ice. The supernatant of the *E. coli* lysate is collected by centrifugation for further use.

2. Static Adsorption Experiment of Caps on Affinity Medium

The DWDLRLLY-6B medium is equilibrated with equilibrating buffer (50 mM PBS, 200 mM NaCl, pH 6.0) for 12 h and then drained. 0.1 g of the medium is weighed out accurately, added to a 25 mL Erlenmeyer flask containing 5 mL of the supernatant of the lysate, and then incubated at 25° C., 170 rpm for 24 h in a shaking bath. The mixture is centrifuged at 10,000 rpm for 1 mM and the supernatant is taken for SDS-PAGE analyses. It is shown that almost all Caps in the supernatant of the lysate bind to the affinity peptide medium. In contrast, Caps cannot be adsorbed to a blank medium. At the same time, most impure proteins are retained in the supernatant, demonstrating that the affinity peptide medium can selectively recognize Caps. It should be noted that adsorption at relatively high salinity (200 mM) suggests the domination role of hydrophobic interaction between DWDLRLLY and Caps, which is in accordance with the simulation results.

3. Chromatographic Separation and Purification Experiment

The DWDLRLLY-6B affinity medium is loaded into a 1 mL glass column (Tricorn 5×5) by gravity sedimentation. The equilibrating buffer (50 mM PBS, 200 mM NaCl, pH 7.0) is used for elution until the baseline is level. After loading 200 μL of the supernatant of the lysate, the equilibrating buffer is used again for elution until the baseline is level. The bound protein is eluted with eluting buffer (50 mM citrate buffer, pH 3.0) of 5-10 column volumes and the regeneration of the affinity medium is carried out by 2-5 column volumes of regenerating buffer (100 mM Gly-HCl, pH 2.4) after the elution peak is separated completely. Equilibrating, washing, elution and regeneration are all performed at the flow rate of 0.5 mL/min while that of 0.2 mL/min is applied for loading. Components of the flow-through peak and the elution peak of the separated supernatant of the *E. coli* lysate are subjected to SDS-PAGE. The electrophoresis image is analyzed by the software Gel-Pro Analyzer 3.1 to determine the purity of VP1. The results indicate that the affinity medium could dramatically improve the purity of VP1 from the supernatant of the *E. coli* lysate from 15.6% to 70.1% by one-step chromatographic purification.

Therefore, the experiments indicate that the affinity peptide ligand DWDLRLLY could effectively purify target proteins and thus is a high-affinity peptide ligand for MPV Caps. It should be noted that, all the 6859 sequences of the peptide ligand library are able to be affinity peptide ligands of Caps in theory as they all have identical design thinking (key residues of VP2-C: D286, W287, L289, 1293, and Y296) and structural features. According to the available experimental data, the affinity peptide ligands in the peptide library are predicated to be effective affinity ligands of MPV Caps.

The invention provides novel affinity peptide ligands of mouse polyomavirus capsomers and a designed screening method thereof. The top one affinity peptide ligand DWDLRLLY is experimentally validated to be an effective affinity ligand of Caps and is capable of further separating and purifying Caps from the supernatant of the *E. coli* lysate, thereby having a broad application prospect in preparation of virus-like particles. However, it should be noted that there also exist some problems in DWDLRLLY, such as too strong hydrophobicity. Thereafter, to obtain higher-affinity and -specificity ligands, modifications of the DWDLRLLY and other peptides in the library are required in the following experiments. A modification strategy includes: adding one or more amino acids to the N/C-terminus of the peptides; inserting one or more amino acids between adjacent residues in the peptides; and replacing certain one or more residues in the peptides with other amino acids.

The invention claimed is:

1. Novel affinity peptide ligands of mouse polyomavirus capsomers, comprising DWDLRLLY (SEQ ID No: 1), DWDLRLIY (SEQ ID No: 2), DWNLRLIY (SEQ ID No: 3), DWFLNLFY (SEQ ID No: 4), DWSLKLVY(SEQ ID No: 5), DWSLRLKY (SEQ ID No: 6) and DWNLHLPY (SEQ ID No: 7).

2. A designed screening method of the novel affinity peptide ligands of the mouse polyomavirus capsomers of claim 1, wherein a novel peptide ligand library of the capsomers is constructed on the basis of the crystal structure of a capsomer and VP2-C complex existing in the natural world, with the feature sequence being DWXLXLXY, wherein the 'X' denotes 19 amino acids except cysteine.

3. The designed screening method of claim 2, wherein the molecular interaction mechanism of the capsomer and VP2-C complex is examined using a molecular mechanics-Poisson-Boltzmann surface area (MM/PBSA) method, where hydrophobic interaction is identified as the major driving force while V283, P285, D286, W287, L289, L293, and Y296 are identified as key residues, making significant contribution to binding, in VP2-C.

4. The designed screening method of claim 2, wherein the peptide library is constructed on the basis of five key residues in VP2-C, i.e., D286, W287, L289, L293, and Y296; and within the range of the peptide library, a candidate peptide modular library is constructed using an amino acid locating method.

5. The designed screening method of claim 2, wherein the high-affinity peptide ligands of the mouse polyomavirus capsomers are screened by molecular docking screening, root mean square deviation (RMSD) comparison, and molecular dynamics (MD) simulation coupled with free energy calculation.

6. The designed screening method of claim 5, wherein the peptide ligands in the peptide ligand library are sequentially docked to the mouse polyomavirus capsomers by molecular docking software VINA, and a total of 1158 peptide ligands with binding free energy less than −6.5 kcal/mol are selected.

7. The designed screening method of claim 6, wherein the RMSD values between the 1158 peptide ligands obtained from docking by VINA and the corresponding key residues in VP2-C are calculated by a program g_rms provided by molecular simulation software GROMACS, and 334 peptide ligands are selected for researching.

8. The designed screening method of claim 7, wherein the 334 peptide ligands are then rescreened on the basis of the C-terminus orientation, and 227 peptide ligands having the similar orientation with VP2-C are selected and rescreened by a docking experiment ROSETTA FlexPepDock, and then ten optimal peptide ligands are selected for MD simulations.

9. The designed screening method of claim 8, wherein the ten optimal peptide ligands obtained by screening are subjected to MD simulations with the complex of the mouse polyomavirus capsomers, and free energy calculation is conducted using the MM/PBSA method to further evaluate the affinity and specificity of the peptide ligands, thereby obtaining seven peptide ligands with relatively high affinity, which are DWDLRLLY (SEQ ID No: 1), DWDLRLIY (SEQ ID No: 2), DWNLRLIY (SEQ ID No: 3), DWFLN-LFY (SEQ ID No: 4), DWSLKLVY(SEQ ID No: 5), DWS-LRLKY (SEQ ID No: 6) and DWNLHLPY (SEQ ID No: 7).

10. Application of the designed screening method of claim 2, wherein a modification strategy for the peptide library includes: adding one or more amino acid residues to the N-terminus; introducing one or more amino acid residues to the C-terminus; inserting one or more amino acid residues between adjacent residues of the peptides; replacing certain one or more resides in the peptides with other amino acid residues.

11. Application of the designed screening method of claim 5, wherein a modification strategy for the peptide library includes: adding one or more amino acid residues to the N-terminus; introducing one or more amino acid residues to the C-terminus; inserting one or more amino acid residues between adjacent residues of the peptides; replacing certain one or more resides in the peptides with other amino acid residues.

* * * * *

SEQUENCE LISTING

```
<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: peptide

<400> SEQUENCE: 1

Asp Trp Asp Leu Arg Leu Leu Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: peptide

<400> SEQUENCE: 2

Asp Trp Asp Leu Arg Leu Ile Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: peptide

<400> SEQUENCE: 3

Asp Trp Asn Leu Arg Leu Ile Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: peptide

<400> SEQUENCE: 4

Asp Trp Phe Leu Asn Leu Phe Tyr
1               5

<210> SEQ ID NO 5
<211> LENGTH: 8
<212> TYPE: PRT
```

```
<213> ORGANISM: Artificial Sequence
<220> FEATURE:
<223> OTHER INFORMATION: peptide

<400> SEQUENCE: 5

Asp Trp Ser Leu Lys Leu Val Tyr
1               5

<210> SEQ ID NO 6
<211> LENGTH: 8
<212> TYPE: PRT
<213> ORGANISM: Artificial Sequence
<220> FEATURE:
<223> OTHER INFORMATION: peptide

<400> SEQUENCE: 6

Asp Trp Ser Leu Arg Leu Lys Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: peptide

<400> SEQUENCE: 7

Asp Trp Asn Leu His Leu Pro Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (3)..(3)
<223> OTHER INFORMATION: Xaa can be any naturally occurring amino acid
      except cysteine
<220> FEATURE:
<221> NAME/KEY: misc_feature
<222> LOCATION: (5)..(5)
<223> OTHER INFORMATION: Xaa can be any naturally occurring amino acid
      except cysteine
<220> FEATURE:
<221> NAME/KEY: misc_feature
<222> LOCATION: (7)..(7)
<223> OTHER INFORMATION: Xaa can be any naturally occurring amino acid
      except cysteine

<400> SEQUENCE: 8

Asp Trp Xaa Leu Xaa Leu Xaa Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: peptide

<400> SEQUENCE: 9

Asp Trp Gly Leu Lys Leu Ile Tyr
1               5

<210> SEQ ID NO 10
<211> LENGTH: 8
```

```
<212> TYPE: PRT
<213> ORGANISM: Artificial Sequence
<220> FEATURE:
<223> OTHER INFORMATION: peptide

<400> SEQUENCE: 10

Asp Trp Gly Leu Arg Leu Lys Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: peptide

<400> SEQUENCE: 11

Asp Trp Ser Leu Asp Leu Trp Tyr
1               5
```